(12) United States Patent
Myles

(10) Patent No.: US 8,945,945 B1
(45) Date of Patent: *Feb. 3, 2015

(54) SAMPLE COLLECTION AND ANALYSIS

(71) Applicant: IDEXX Laboratories, Inc., Westbrook, ME (US)

(72) Inventor: Matthew Howard Myles, Moberly, MO (US)

(73) Assignee: IDEXX Laboratories, Inc., Westbrook, ME (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/538,381

(22) Filed: Nov. 11, 2014

Related U.S. Application Data

(63) Continuation of application No. 14/089,103, filed on Nov. 25, 2013.

(60) Provisional application No. 61/776,560, filed on Mar. 11, 2013.

(51) Int. Cl.
*G01N 33/543* (2006.01)

(52) U.S. Cl.
USPC ............. 436/518; 435/7.1; 435/7.92; 436/63; 436/811

(58) Field of Classification Search
None
See application file for complete search history.

(56) References Cited

U.S. PATENT DOCUMENTS

2005/0108048 A1   5/2005   Taft et al.

OTHER PUBLICATIONS

Beaudette, P., et al., "Discovery stage pharmacokinetics using dried blood spots", Journal of Chromatography, 809:153-158 (2004).
Henderson, K., et al., "Efficacy of Direct Detection of Pathogens in naturally Infected mice by Using a High-Density PCR Array", Journal of American Association for Laboratory Animal Science, 52:1-10 (Nov. 2013).
Mei, J., et al., "Use of Filter Paper for the Collection and Analysis of Human Whole Blood Specimens", Journal of Nutrition, 131:1631S-1636S (2001).
Wunderlich, M., et al., "Multiplexed Fluorometric ImmunoAssay Testing methodology and Troubleshooting", Journal of Visualized Experiments, 58:e3715, 1-7 (2011).
Bioanalytical Services Dried Blood Spot Technical Sheet, Charles River Laboratories International, Inc. (2010).
Manchester Medical Blood Collection Card, design date Jul. 8, 2011.
Sheffield Microbiology Card, design date Aug. 25, 2011.
Health Monitoring, Harlan Laboratories, 2008.
Brookes, S., Dry Blood Spots: A Technique Overview [online] Charles River, 2011 [retrieved on May 5, 2014]; http:/www.criver.com/customer-service/education-training/educations/2011/01/dry-blood-spots time stamps 0:52, 1:08, 1:37, 1:39, 1:40, 6:55, 11:08, 11:35, 11:51, 11:56, 12:52 and 15:47, Jan. 31, 2011.
Facial Vein Technique [online] www.ahc.umn.edu; The University of Minnesota; http://ww.ahc.umn.edu/rar/facial_vein.html; 2006 [retrieved on May 15, 2014].
Specimen Collection and Shipping Instructions, www.usbioteck.com; US Bio Tek, 2009.
Li, et al., "Perforated Dried Blood Spots: A Novel Format for Accurate Microsampling", Bioanalysis, 3:2321-2333 (2011).
Li, et al.,Perforated Dried Blood Spot Accurate Microsampling: the concept and its applications in toxicokinetic sample collection, J. Mass. Spectrom. 2012, 47, 655-667.
Kehler, et al., "Application of DBS for quantitative assessment of the peptide Exendin-4; comparison of plasma and DBS method by UHPLC-MS/MS", Bioanalysis, 2(8), 2010, pp. 1461-1468.
Research Committees, Boston University, Rodent Breeding Colony Management—Mice, Oct. 2010, pp. 1-5.
Williams, et al., The use of dried blood spot sampling in the National Social Life, Health and Aginging Project, Journal of Gerontology; Social Sciences, 64B(S1), pp. i131-i136, 2009.
Olfert, et al., Humane Endpoints for Infectious Disease Animal Models, ILAR Journal, vol. 41, No. 2, 2000, pp. 99-104.
Brown, et al., Detection of CMV and EBV from Dried Blood Spots Using Automated Nucleic Acid Extraction and Lyophilised Real-Time PCR Reagents for the Home Monitoring of Renal Patients Post Transplant; Abstract P-096, 15th Annual Meeting of the European Society of Clinical Virology, Madrid, Sep. 25, 2012.
Brown, et al., Assessment of the detection of CMV and EBV from Dried Blood Spots Using Automated Nucleic Acid Extraction and Lyophilised Real Time PCR Reagents for the home monitoring of renal patients post transplant; Poster No. P-096, 15th Annual Meeting of the European Society of Clinical Virology, Madrid, Sep. 25, 2012.
IDEXX RADIL, Guide to Optimal Health Monitoring, 2011.
IDEXX RADIL, Opti-Q Panels Brochure, Oct. 2012.

*Primary Examiner* — Gary W Counts
(74) *Attorney, Agent, or Firm* — McDonnell Boehnen Hulbert & Berghoff LLP

(57) ABSTRACT

Management of the health status of an animal colony using a plurality of blood collection cards and the analysis of dried blood from members of the colony that has been collected on the cards. Members of the colony may be removed from the colony as a result of the analysis.

21 Claims, 3 Drawing Sheets

Figure 1A
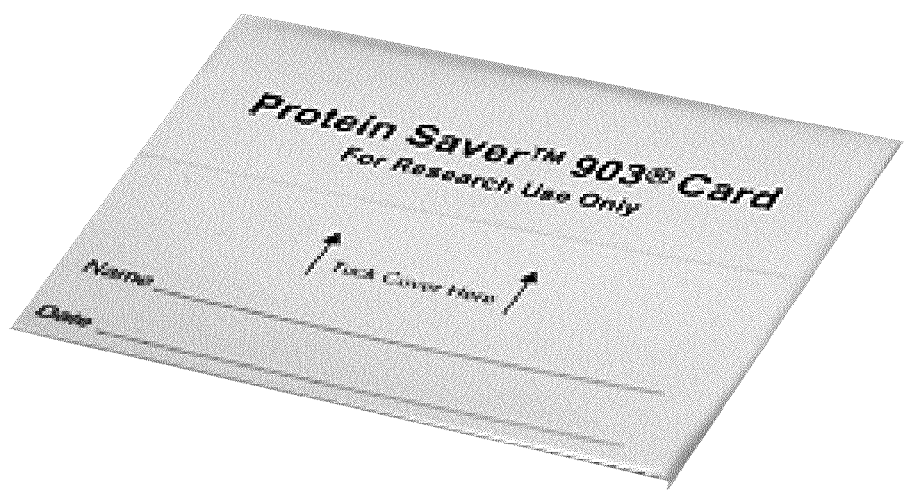
Figure 1B
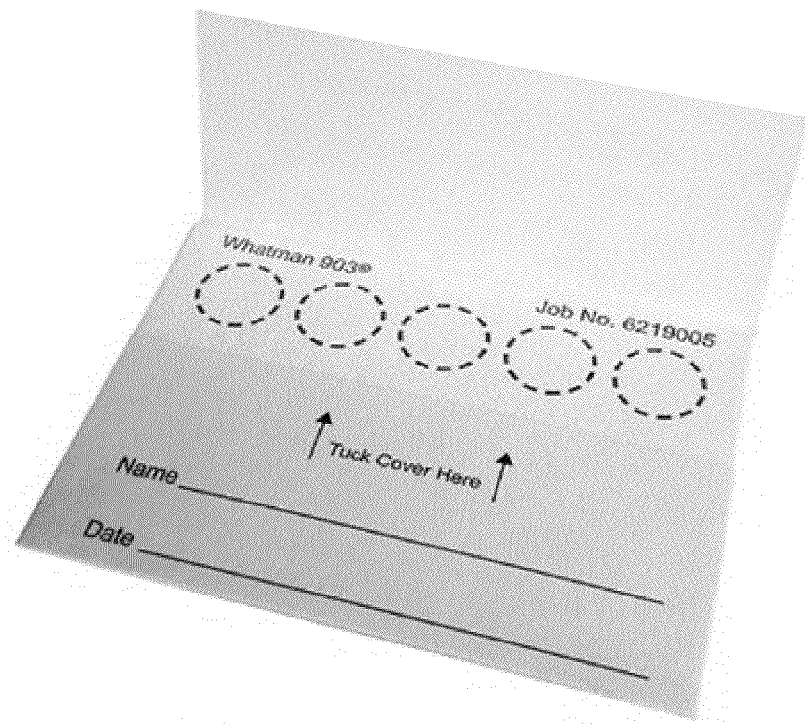

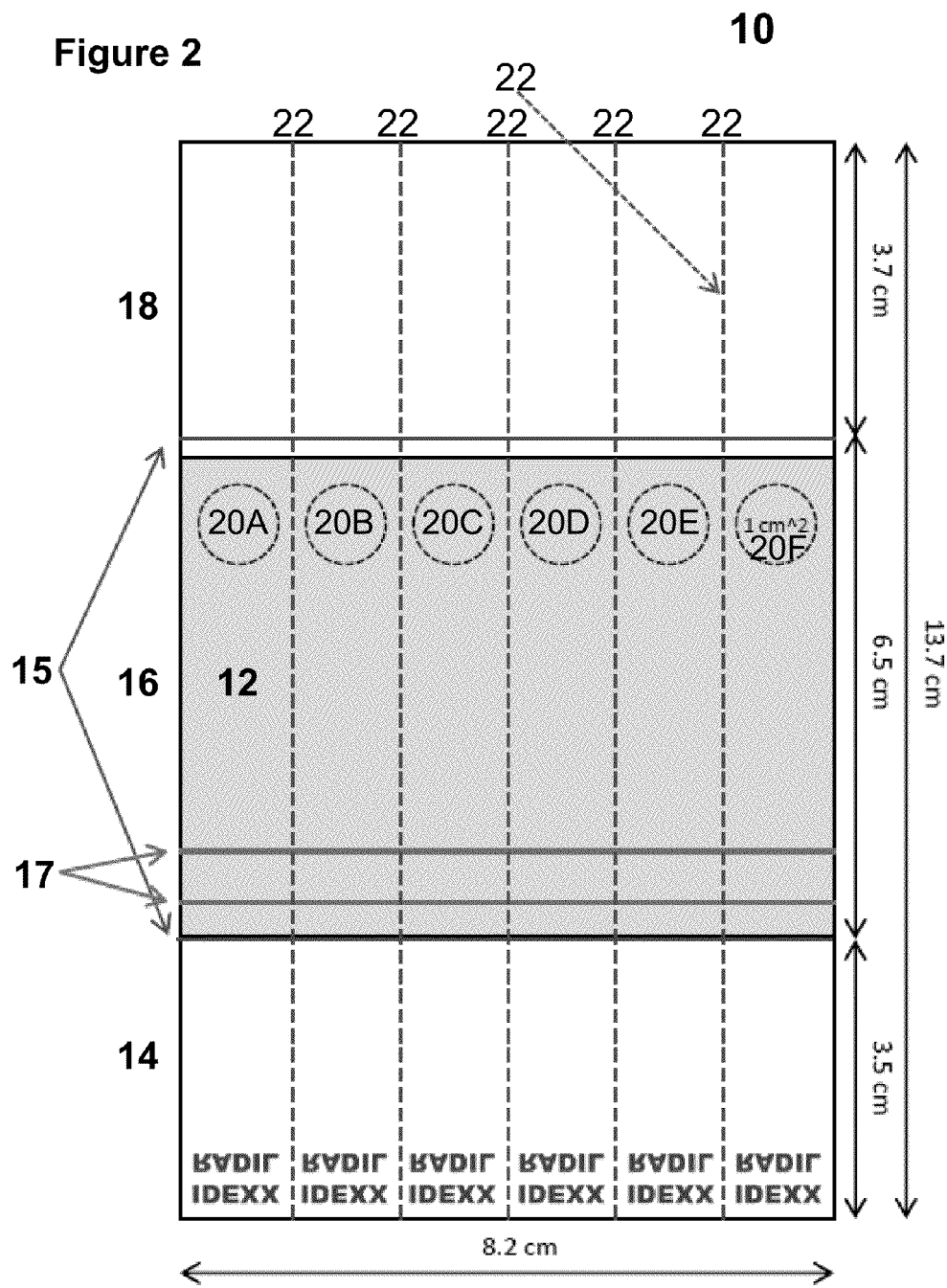

SAMPLE COLLECTION AND ANALYSIS

RELATED APPLICATIONS

This application is a continuation application of U.S. patent application Ser. No. 14/089,103, filed Nov. 25, 2013, which claims the benefit of U.S. Provisional Application No. 61/776,560, filed Mar. 11, 2013.

FIELD

The invention relates to the collection and analysis of biological samples from populations of animals. More particularly, the invention is directed to the management of animal colonies using dried blood samples from the members of the colony for analysis of disease or phenotype of the colony.

BACKGROUND

Over the past five decades, great strides have been made in the identification and eradication of infections from laboratory rodents. As a result, most contemporary biomedical research rodent colonies are relatively free of the pathogenic viruses, parasites, bacteria, and fungi that cause clinical disease. However, some microbes, especially those agents that cause subclinical disease, remain in an enzootic state in many research colonies. These agents, despite their insidious nature, have an impact on physiologic parameters of the host and thus on the results of animal experiments, independent of their pathogenic potential. Therefore, timely and accurate diagnosis of infectious disease in animal research models is critical to the success of biomedical research. To this end, institutional veterinarians closely monitor the health of research animals through periodic systematic examination of sample groups of research animals against a predetermined list of infectious agents. Rodent health monitoring can generally be accomplished using a combination of molecular and serological diagnostic assays. Molecular diagnostic tools provide a real-time assessment of infection; whereas, serological tools detect the presence of antibodies to infectious agents, thus, providing an historical perspective of infectious disease exposure over the life of the animal.

The current practice for collection of blood or serum for serological evaluation of infectious disease in laboratory animals includes: most commonly, euthanasia of animals for collection of at least 100 µL of blood by cardiocentesis. Once collected the whole blood sample is allowed to clot, which typically requires 2-12 hours, then whole blood is centrifuged and the serum is separated from the cellular (clotted) fraction. Next, the serum is shipped to a facility at refrigerated or frozen temperatures using an overnight service (generally one or two pounds of ice packs are required) in a STRYOFOAM™ shipping box.

This practice is inconvenient and expensive in light of the amount of animal colonies and the number of analytes that must be tested to ensure colony health and homogeneity. Accordingly, the inventors have identified a need in the art to provide a simplified and efficient method for sample collection and analysis to ensure cost effective colony management.

SUMMARY

In one aspect, the disclosure is directed to a method for managing a an animal colony. The method includes collecting blood samples from a plurality of members of the colony on a plurality of collection cards; allowing the blood samples to dry on the collection cards; transporting the collection cards to a laboratory as a single unit; extracting the samples from the cards; analyzing the samples for the presence or absence of a biological marker; and removing one or more of the members from the colony based upon the presence or absence of the marker in the samples from the one or more members. The biological marker may be a marker for an infectious disease.

In various aspects of the disclosure each collection card in the plurality of collection cards is labeled to identify the member of the population associated with each sample on a card. The samples may be analyzed in a multiplex immunoassay, for example, and immunoassay that detects at least ten different analytes in the samples. Each collection card may contain segments for collecting up to, for example, five samples, fifty samples, or 100 samples. The volume of blood of each sample collected on the card may be about 10-40 µL. Blood may be collected from the animal's lateral saphenous vein, facial vein or temporal vein, and the blood may be collected on the card without a collection device. The samples may be dried and/or shipped at room temperature.

In a further aspect, the disclosure is directed to method of determining the health status in a population of rodents. The method includes providing a plurality of blood collection cards; instructing the user to draw blood from an individual rodent; instructing the user to apply the blood to one of the plurality of blood collection cards; instructing the user to allow the blood sample to dry on the collection card; instructing the user to repeat the blood collection and drying at least once to provide a plurality of blood collection cards spotted with blood from the population of rodents; instructing the user to transport the plurality of collection cards to a laboratory as a single unit; extracting the samples from the cards; analyzing the samples for the presence or absence of at least one biological marker for an infectious disease; and reporting the results of the analysis back to the user.

In various aspects, the members of the population of rodents are mice, and the user is instructed to draw the blood from a facial vein. In another aspect, the members of the population of rodents are rats.

BRIEF DESCRIPTION OF THE FIGURES

FIGS. 1A and 1B shows an example of a prior art sample collection card.

FIG. 2 shows an example of a sample collection card having six spots for sample collection that can be separated (if desired) by detachment along various perforations.

DETAILED DESCRIPTION

Figure 3A:
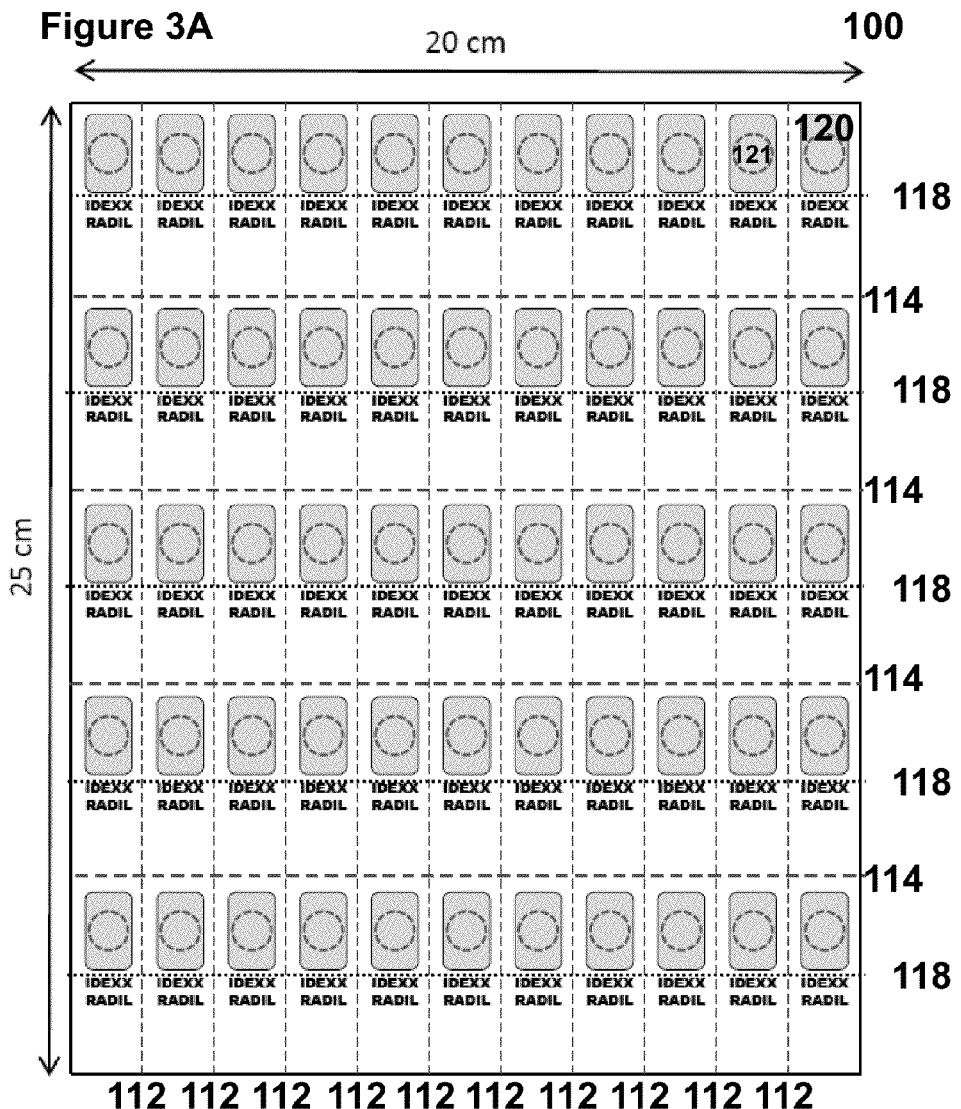
FIGS. 3A and 3B shows a top view of and a side view an example of a sheet having a plurality of sample collection cards that can be separated (if desired) by detachment along various perforations.

The invention addresses the challenges associated with the collection, identification and processing of voluminous numbers of samples obtained from animal colonies, and in particular rodent colonies. These colonies are maintained for research purposes and, in many cases, it is critical that the members of the colonies have particular phenotypes and health status. The testing of individual members of the colonies for up 30 different bacterial and viral agents and for desired phenotypic characteristics may be necessary to ensure the health of the colony and its usefulness in testing, for example, the efficacy of pharmaceutical agents on large populations.

The use of the invention requires significantly less sample from colony members than traditional sampling processes (~25 μL vs. 100 μL), making live (antemortem) sample collection safer, more simple and more feasible (eliminates the need for phlebotomists therefore enabling expanded or self-sampling). Accordingly, in one aspect, the invention provides a library of blood samples from a population of animals. The library includes samples from a plurality of members of a colony. Typically, a statically significant number of animals in the colony are tested for particular phenotype or disease. For example, in very large populations (e.g., up to 100,000 animals) as many to 400 animals are tested (e.g., 2 animals per group of 50). In some populations, all of the animals are tested. Collection of the test samples from the individual members of the colony provides a library of samples representative of the population.

In accordance with the invention, the library of samples is collected on collection cards, which are typically absorbent and inert fibrous thin sheet materials. In one particular embodiment, the collection cards are WHATMAN® FTA® DMPK-C (GE Healthcare Biosciences, Piscataway, N.J.), which have multiple collection areas for samples of about 10-40 μL. In other embodiments, the spots can hold about 20-30 μL, and in another embodiment a 1 cm² collection area holds approximately 25 μL of whole blood. While the cards can be impregnated with various chemicals (e.g., stabilizers, enzyme inhibitors, etc.), it is preferred that the cards contain no impregnated chemicals. It has also been found that use of the cards does not adversely denature target proteins.

An example of a prior art blood collection card is shown in FIGS. 1A and 1B. This card (Protein Saver™ 903® card by Whatman) has five blood collection spots arranged on a continuous, non-perforated web of material. In this embodiment, all blood collection spots are present for purposes of collecting blood from one patient/individual. After blood is spotted and preferably dried, the top cover is tucked into the bottom panel as shown.

In rodent populations, blood is typically drawn from the lateral saphenous vein, facial vein or the temporal vein. In one aspect of the invention, collection is accomplished directly from the vein on to the collection card without the use of a capillary tube or other collection device by contacting the card directly with the animal body at the site of the punctured vein or by permitting a drop of blood to fall onto the desired area of the card. Ideally, a single large drop should touch the card in order to allow the sample to spread quickly and symmetrically on the collection spot of the card surface to provide a reproducible, uniform spot. Using the WHATMAN® FTA® DMPK-C cards, spot formation is not essentially influenced by application speed or direction, and provides minimal chromatographic separation in the card. Spot area is generally proportional to sample volume, which provides uniformity in sample size when the card is "punched" as a first step of sample extraction from the card. In one embodiment, the collection card is WHATMAN® FTA® 31 ETF PK paper.

For use with collection from the saphenous, facial or temporal veins, it is desirable that each card contain only one sample to avoid contamination between samples as the result of the collection of blood from a live animal. When blood is collected directed from the animal, it is spotted without anticoagulant. Analytical labs, however, normally use blood containing EDTA or another anticoagulant for controls and standards. For validated assays it may be necessary to collect data showing the anticoagulant to be unnecessary.

In another aspect, the invention provides that each collection card identify the animal providing the sample. Animal identification can be accomplished by several known means according to animal colony and clinical laboratory management as generally known in the art, including labels and barcodes containing information that can be electronically stored and transmitted. In one embodiment, a plurality of sample spots and room for subject identifying information is provided on a sheet containing segments that include the sample spot and identifying information. Perforations between the spots allow for removal of segments to provide individual collection cards for each subject containing the sample and identification information. For instance, a sheet may include 2 to 100, more particularly 2-10, for example 3, 4, 5, 6, 7, 8, or 9, segments that can be separated prior to or at the time of sample collection.

Once the samples from the colony have been collected, samples are dried, preferably in an environment with good air circulation and low ambient humidity. Moderate heating may be considered, but care should be taken so as not to damage the cards or reduce analyte stability. Fans or vacuum desiccators may speed the process, which generally takes about two hours at room temperature. In another embodiment, the card can be immediately folded to protect the sample without drying first, and without smearing, disturbing or contaminating the sample.

Once the samples are dry, the cards can be arranged to be transported, preferably gathered together as a single unit, for providing information regarding one or more biological markers in the population of animals. In this aspect, the library of samples on the cards can be transported using commercially available transportation and delivery services (e.g., U.S. Mail, FEDEX®, UPS®) in standard delivery envelops without refrigeration to a reference laboratory for analysis. Blood samples collected and dried on the cards are generally stable for up to 7 days at room temperature. Use of a desiccant in the shipping container can help to avoid degradation. In some embodiments, library of collection cards contains up 100, 200, 300 or 400 cards.

FIG. 2 shows a segmented collection card 6 having sample spots. Card 10 has a sample panel 12 (depicted in gray), an identification panel 14, a mid panel 16 and an end panel 18. Optional fold scores are shown at 15. In one embodiment, the sample panel 12 is WHATMAN® FTA® 31 ETF PK paper, while the other panels can be a sturdy card stock such as 100 pound White Tag card stock, for example about approximately 100 pound weight. In one embodiment, the FTA® paper can be the length of the panel 12, while the length of the card stock is that of the panels 14, 16 and 18, wherein the two sections are glued at line 17 where overlapping at panel 12 (FTA® paper preferably on top of the card stock). Card 10 is shown with six target sample circles 20A-F. Lateral perforations 22 can be provided that run across the length of all panels to allow the user to separate the card 10 such that a single sample circle is on each separated card. As mentioned elsewhere in this disclosure, the card can have multiple sample spots and perforations. In use, after the sample(s) is applied, the first panel 18, and then the panel 14, can be folded onto the panel 16 to protect the sample(s) in 20A-F of the panel 12.

Figure 3B:
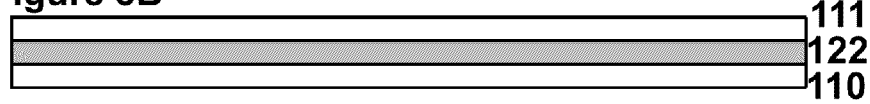

FIG. 3A shows an alternate embodiment of the present invention wherein a sheet having multiple sample collection cards that can be separated (if desired) by detachment along various perforations. FIG. 3B depicts a cross sectional view of a sheet 100 having a base material 110 that is preferably a sturdy card material (such as 100 pound White Tag), which is optionally laminated to the collection material 122. A layer of a blood collection material 122 is preferably glued on top of the base 110 as shown, and a top layer 111 (which is optionally laminated) of the same material as the base material on top of the collection material 122. As with FIG. 2, collection material 122 is any material that can receive and secure a blood sample such as, for example, FTA® paper. The top material 111 has a window 120 (e.g., 1.2 cm×2.0 cm), depicted in gray, which leaves the collection material 122 exposed. The collection material 122 has blood collection target spots 121 printed thereon to facilitate application of the blood sample. The sheet 100 has a plurality of horizontal perforations 114 and a plurality of vertical perforations 112. By way of example only, if sheet 100 is 20 centimeters by 25 centimeters, then 55 individual cards (~5 centimeters by ~1.8 centimeters) can be separated and used for collection of samples from 55 individual subjects. Also shown in FIG. 3A are optional fold lines 118 on sheet 100.

In use, the blood collection cards (each having a single blood collection spot 20 or a spot 121 or more than one blood collection spot) can be separated from card 10 or sheet 100. Information about the blood donor can be applied to the card along with the blood sample. After sample application, the card can be optionally folded to protect the sample and transported to a testing facility. Results of tests run on the blood sample can be matched with the donor and the information transmitted back to the facility (e.g., via e-mail, computer network, internet, in writing, etc.) where the blood sample was taken. In the case of rodent colony testing, one or more tests that show positive for the presence of a non-desirable condition (e.g., infection, see below), may result in the segregation, quarantine and/or euthanasia of rodents in the colony.

The arrangement of the cards does not necessarily require spacers between the cards to avoid contact between dried blood samples. However, it may be desirable to include a flap that can be folded over once or twice so that the sample spot is covered on at least one side of the spot. The flap can ensure that sample spots on different cards are not in direct contact during shipping. As shown in FIG. 2, the cards can contain one or more fold scores or other indications of where the card should be folded to ensure isolation of the spot and, in some instances, allow access to identifying information without unfolding the flap.

At the clinical laboratory, samples are removed from the cards by punching the cards with a punch that provides a core containing a uniform sample size when the sample has been properly collected and the size of the punch is smaller than the sample spots. Typical punch sizes for samples of up to 20 microliters are 3-10 mm. Larger samples representing up to 100 microliters of properly collected blood can be obtained with a larger punch, for example 9 mm. If capturing total sample volume is desirable over uniformity of sample size, a punch larger than the spots, or scissors, can be used to ensure that the core contains the entire sample volume.

Once the sample has been punched from the cards, the samples can be extracted from the core using known solvents. For small molecules, the solvent can be anything that is a solvent for the analyte. Methanol and acetonitrile are widely used, either straight or mixed with water. Water itself may also be used for extremely polar analytes. Extraction of ionizable analytes is often improved by pH adjustment—increasing the charge to improve solubility in water or reducing it to promote solubility in organic solvents. In some instances, extraction of even moderately polar analytes is increased by adding perhaps 10-15% water to methanol, sometimes by adding water to the dry spot first, then allowing to soak a few minutes before adding organic solvent. An extremely hydrophobic analyte may be best extracted with a nonpolar solvent such as hexane, also providing some cleanup by leaving polar contaminants undissolved in the punch.

For peptides and proteins, aqueous buffers with pH and salt concentration to promote protein stability can be used. The addition of a non-ionic detergent, such as 0.1% TWEEN™-20 or TRITON™ X-100 detergents may be desirable. Removal may require incubation with gentle mixing for one to several hours. Hydrophobic peptides will probably extract better with some methanol or acetonitrile added.

In on embodiment, a 9 mm punch is removed, using an appropriate 9 mm single hole punch, from the card, placed in a sterile tube. Antibodies are eluted with 100 microliters of buffer containing Tris-buffered saline with 1 mM EDTA. The tube is placed in the refrigerator overnight to allow efficient antibody elution from the membrane.

Once the library samples are extracted, the samples are analyzed for the presence or absence of a biological marker. For example, mouse colonies can be tested for the following infectious agents, and the samples may be tested in various subsets (panels) as exemplified in Table 1.

TABLE 1

| | Mouse Panel | | | | | |
| --- | --- | --- | --- | --- | --- | --- |
| Test | A | B | C | D | E | F |
| MHV | X | X | X | X | X | X |
| MVM (MMV) | X | X | X | X | X | X |
| NS1 (Generic Parvovirus) | X | X | X | X | X | X |
| MPV (MPV 1-5) | X | X | X | X | X | X |
| MNV | X | X | X | X | X | X |
| TMEV | X | X | X | X | X | X |
| EDIM | X | X | X | X | X | X |
| Sendai virus | | X | X | X | X | X |
| *Mycoplasma pulmonis* | | X | X | X | X | X |
| PVM | | | X | X | X | X |
| REO3 | | | X | X | X | X |
| LCMV | | | X | X | X | X |
| Ectromelia virus | | | X | X | X | X |
| MAD1 | | | | X | X | X |
| MAD2 | | | | X | X | X |
| Polyoma virus | | | | X | X | X |
| *Encephalitozoon cuniculi* | | | | | X | X |
| CARB | | | | | X | X |
| *Clostridium piliforme* | | | | | X | X |
| MCMV | | | | | X | X |
| K virus | | | | | | X |
| Hantaan virus | | | | | | X |
| Lactate dehydrogenase-elevating virus | | | | | | X |
| MTV(IFA) | | | | | | X |

Similarly, for rat colonies, the analytes and panels are exemplified in Table 2.

TABLE 2

| | Rodent Panel | | | | |
| --- | --- | --- | --- | --- | --- |
| Test | A | B | C | D | E |
| RCV | X | X | X | X | X |
| NS1 (Generic Parvovirus) | X | X | X | X | X |
| RPV | X | X | X | X | X |
| RMV | X | X | X | X | X |
| KRV | X | X | X | X | X |
| H-1 | X | X | X | X | X |
| RTV (Rat theilovirus) | X | X | X | X | X |
| Sendai virus | | X | X | X | X |
| PVM | | X | X | X | X |
| *Mycoplasma pulmonis* | | X | X | X | X |
| REO3 | | | X | X | X |
| LCMV | | | X | X | X |
| CARB | | | | X | X |
| Hantaan virus | | | | X | X |
| *Clostridium piliforme* | | | | X | X |
| MAD1 | | | | X | X |

TABLE 2-continued

| | Rodent Panel | | | | |
|---|---|---|---|---|---|
| Test | A | B | C | D | E |
| MAD2 | | | | | X |
| *Encephalitozoon cuniculi* | | | | | X |
| IDIR | | | | | X |

Animal colonies of other species can be analyzed for panels of markers appropriate for the species.

Overall sensitivity for small molecules is very much a function of analyte, matrix interferences, chromatography conditions and mass spectrometer capabilities. In general, values in the range of 0.1-10 ng/mL can be obtained from single 3 mm punches. Proteins can be extracted from blood spots and detected by immunoassay with sensitivity comparable to standard plasma or serum samples.

In one aspect, the extracted samples are analyzed in a Multiplex Fluorescent Immunoassay (MFI) that is based both on bead-based immunoassay and flow cytometry. Purified antigen or control preparations are covalently linked to one of, for example, 100 different types of polystyrene beads, which vary slightly in the intensity of their color. If IgG antibody to a particular antigen is present, then it will bind to the antigen on a specific bead and will then be detected by subsequent binding of goat anti-species antibody conjugated to a fluorochrome (e.g., R-phycoerythrin). The reader channels single beads through a dual laser detector which simultaneously determines both the bead type by the internal dye combination and the fluorescent intensity associated with each individual bead. The fluorescent intensity associated with each of the individual beads of each type are used in the determination of each MFI value. Side-by-side testing of thousands of individual results from hundreds of samples show overall correlation between MFI and ELISA is greater than 99.5% for both mouse and rat samples. In general, MFI is more sensitive than ELISA and is less prone to false positive results. MFI requires only 1.0 µL of undiluted serum (5.0 µL of 1:5 diluted serum) regardless of the number of tests requested.

The ability to use small sample sizes for testing several analytes in a sample using MFI sample coupled with the invention including library of sample collection cards allows for the comprehensive and convenient analysis of a colony of survival-bled (antemortem) animals. The results of the colony analysis can be transmitted directed to the colony manager by electronic communications, including e-mail and smart phone applications, so that that laboratory manager has immediate access to data regarding the colony or individual room of a colony.

In other embodiments, the eluant is then evaluated by other know immunoassay techniques known to those of skill in the art (e.g., IFA and western blot).

In one aspect, the invention is directed to a method of managing a rodent colony. The method analysis of biological markers for disease or phenotype within the colony using sample collection cards, and sample collection and analysis as described herein. Colony management may include removing members from the colony that test positive or negative for the biological marker.

The following are provided for exemplification purposes only and are not intended to limit the scope of the invention described in broad terms above. All references cited in this disclosure are incorporated herein by reference.

EXAMPLES

Example 1

Monitoring a Rodent Colony for Infectious Agents

Routine rodent health monitoring for infectious agent exposure is accomplished by serologically evaluating rodent serum samples for the presence of antibodies formed as part of the immune response to infection. To accomplish this, blood is collected, via venipuncture, from sample groups of research animals (e.g., ~10% of the rodent colony of interest) and spotted onto membrane cards labeled with unique animal identification codes to allow for later identification of the animal. Once the blood samples from the rodent research colony have been collected and samples are dried, the cards are transported, using commercially available transportation and delivery services (e.g., U.S. Mail, FEDEX® or UPS®) in standard delivery envelops without refrigeration, to a reference laboratory for analysis. Samples are tested against a predetermined list of indicators (see for example Table 1 and Table 2) of an infection and results are reported to the submitter. When an infectious disease outbreak is detected, the infected animals are identified using the unique identification codes and quarantined. Additional steps may be taken to ascertain the extent of the outbreak and to eliminate/control the infectious agent. Ultimately, it may be necessary to re-derive or restock the colony with disease-free animals.

Although various specific embodiments of the present invention have been described herein, it is to be understood that the invention is not limited to those precise embodiments and that various changes or modifications can be affected therein by one skilled in the art without departing from the scope and spirit of the invention. The examples given above are merely illustrative and are not meant to be an exhaustive list of all possible embodiments, applications or modifications of the invention. Thus, various modifications and variations of the described invention will be apparent to those skilled in the art without departing from the scope and spirit of the invention. Although the invention has been described in connection with specific embodiments, it should be understood that the invention as claimed should not be unduly limited to such specific embodiments. Indeed, various modifications of the described modes for carrying out the invention which are obvious to those skilled in animal colony management, molecular biology, immunology, chemistry, biochemistry or in the relevant fields are intended to be within the scope of the appended claims.

Any numerical values recited herein include all values from the lower value to the upper value in increments of one unit provided that there is a separation of at least two units between any lower value and any higher value. As an example, if it is stated that the concentration of a component or value of a process variable such as, for example, size, angle size, pressure, time and the like, is, for example, from 1 to 90, specifically from 20 to 80, more specifically from 30 to 70, it is intended that values such as 15 to 85, 22 to 68, 43 to 51, 30 to 32, etc. are expressly enumerated in this specification. For values that are less than one, one unit is considered to be 0.0001, 0.001, 0.01 or 0.1 as appropriate. These are only examples of what is specifically intended and all possible combinations of numerical values between the lowest value and the highest value enumerated are to be considered to be expressly stated in this application in a similar manner.

The disclosures of all references and publications cited herein are expressly incorporated by reference in their entireties to the same extent as if each were incorporated by reference individually.

What is claimed is:

1. A method of determining a presence or absence of an infectious disease in a population of rodents, the method comprising:
   (a) providing instructions to a user responsible for a population of animals comprising the following:
      (i) draw blood from an individual rodent;
      (ii) apply the blood to one of a plurality of blood collection cards;
      (iii) allow the blood sample to dry on the collection card;
      (iv) repeat steps i, ii, and iii at least once to provide the plurality of blood collection cards spotted with blood from a plurality of members from the population of rodents; and
      (v) transport the plurality of collection cards to a laboratory as a single unit;
   (b) receiving the plurality of collection cards as a single unit from the user,
   (c) extracting dried blood from the cards;
   (d) conducting an immunoassay for analyzing the extracted blood for a presence or absence of at least one antibody for an infectious agent indicative of an infectious disease, thereby determining the presence or absence of the infectious disease in the population; and
   (e) reporting the results of the presence or absence of the infectious disease to the user.

2. The method of claim 1, wherein the immunoassay comprises contacting the extracted blood with a fluorescently labeled binding partner for the antibody.

3. The method of claim 1, wherein the immunoassay is a multiplex fluorescence immunoassay.

4. The method of claim 1, wherein the members of the population of rodents are mice.

5. The method of claim 4, wherein the instruction to draw blood includes instructing the user to draw the blood from a facial vein.

6. The method of claim 1, wherein the members of the population of rodents are rats.

7. The method of claim 1, wherein the instructions further comprise, prior to instruction (v), the following instruction: identify at least one of the rodent population and the individual rodent on each of the plurality of blood collection cards.

8. The method of claim 1, wherein the blood collection cards each have at least one collection area having an absorbent material suitable for holding about 10-40 µL of whole blood.

9. The method of claim 1, wherein the blood collection cards each have at least two collection areas.

10. The method of claim 9, wherein the at least two collection areas are separated by a perforation that allows separation of the cards such that a single sample area is on each separated card.

11. The method of claim 4, wherein the step of analyzing the extracted blood comprises analyzing for the presence or absence of seven or more diseases selected from the group consisting of:
   a. MHV;
   b. MVN (MMV);
   c. NS1 (Generic Parvovirus);
   d. MPV (MPV1-5);
   e. MNV;
   f. TMEV;
   g. EDIM;
   h. Sendai virus;
   i. *Mycoplasma pulmonis;*
   j. PVM;
   k. REO3;
   l. LCMV;
   m. Ectromelia virus;
   n. MAD1;
   o. MAD2;
   p. Polyoma virus;
   q. *Encephalitozoon cuniculi;*
   r. CARB;
   s. *Clostridium piliforme;*
   t. MCMV;
   u. K virus;
   v. Hantaan virus;
   w. Lactate dehydrogenase-elevating virus; and
   x. MTV.

12. The method of claim 6, wherein the step of analyzing the extracted blood comprises analyzing for the presence or absence of seven or more diseases selected from the group consisting of:
   a. RCV;
   b. NS1 (Generic Parvovirus);
   c. RPV;
   d. RMV;
   e. KRV;
   f. H-1;
   g. RTV (Rat theilovirus);
   h. Sendai virus;
   i. PVM;
   j. *Mycoplasma pulmonis;*
   k. REO3;
   l. LCMV;
   m. CARB;
   n. Hantaan virus;
   o. *Clostridim piliforme;*
   p. MAD1;
   q. MAD2;
   r. *Encephalitozoom cuniculi;* and
   s. IDIR.

13. The method of claim 3, wherein the members of the population of rodents are mice.

14. The method of claim 3, wherein the instruction to draw blood includes instructing the user to draw the blood from a facial vein.

15. The method of claim 3, wherein the members of the population of rodents are rats.

16. The method of claim 3, wherein the instructions further comprise, prior to instruction (v), the following instruction: identify at least one of the rodent population and the individual rodent on each of the plurality of blood collection cards.

17. The method of claim 3, wherein the blood collection cards each have at least one collection area having an absorbent material suitable for holding about 10-40 µL of whole blood.

18. The method of claim 3, wherein the blood collection cards each have at least two collection areas.

19. The method of claim 18, wherein the at least two collection areas are separated by a perforation that allows separation of the cards such that a single sample area is on each separated card.

20. The method of claim 13, wherein the step of analyzing the extracted blood comprises analyzing for the presence or absence of seven or more diseases selected from the group consisting of:

a. MHV;
b. MVN (MMV);
c. NS1 (Generic Parvovirus);
d. MPV (MPV1-5);
e. MNV;
f. TMEV;
g. EDIM;
h. Sendai virus;
i. *Mycoplasma pulmonis;*
j. PVM;
k. REO3;
l. LCMV;
m. Ectromelia virus;
n. MAD1;
o. MAD2;
p. Polyoma virus;
q. *Encephalitozoon cuniculi;*
r. CARB;
s. *Clostridium piliforme;*
t. MCMV;
u. K virus;
v. Hantaan virus;
w. Lactate dehydrogenase-elevating virus; and
x. MTV.

21. The method of claim 15, wherein the step of analyzing the extracted blood comprises analyzing for the presence or absence of seven or more diseases selected from the group consisting of:
a. RCV;
b. NS1 (Generic Parvovirus);
c. RPV;
d. RMV;
e. KRV;
f. H-1;
g. RTV (Rat theilovirus);
h. Sendai virus;
i. PVM;
j. *Mycoplasma pulmonis;*
k. REO3;
l. LCMV;
m. CARB;
n. Hantaan virus;
o. *Clostridim piliforme;*
p. MAD1;
q. MAD2;
r. *Encephalitozoom cuniculi;* and
s. IDIR.

* * * * *